Jan. 6, 1948. C. KETTEN Plant Pat. 774
ROSE PLANT
Filed Dec. 30, 1942
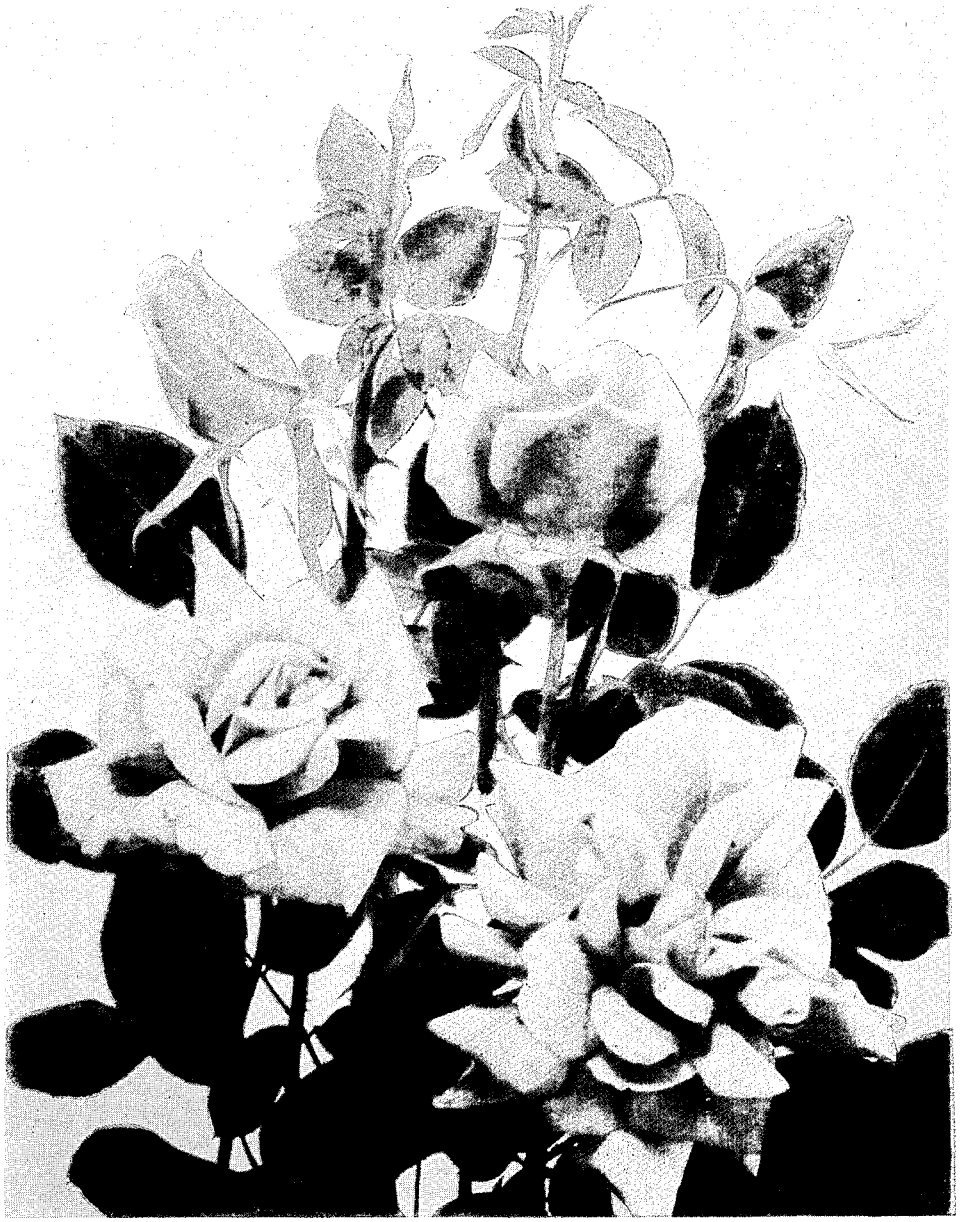
Inventor
Charles Ketten
By Robb & Robb
Attorneys.

Patented Jan. 6, 1948

Plant Pat. 774

UNITED STATES PATENT OFFICE

774

ROSE PLANT

Charles Ketten, Luxemburg, Luxemburg; Marguerite Ketten, administratrix of said Charles Ketten, deceased, assignor to the Conard-Pyle Company, West Grove, Pa., a corporation of Pennsylvania Application December 30, 1942, Serial No. 470,708

1 Claim. (Cl. 47—61)

The present invention relates to a new and distinct variety of hybrid tea rose plant adapted particularly for garden decoration.

While this new rose has many novel characteristics, its primary claim to distinctiveness is found in the coloring of its flowers, comprising a harmonious combination of red tones extending from its outer to its inner petals and differing on opposing surfaces of the petals, such coloring gradually changing with the development of the flower to maturity.

Additionally, the new rose is characterized as to novelty by the unusual length of the bud, its strong stems, large size of its flowers, and good vegetative habit.

More specifically, the features of this new variety are set forth as follows, the color terminology being in accord with Ridgway's Color Standard:

Type: Hardy; tall bush; outdoor; for garden decoration.

Class: Hybrid tea.

Propagation: Holds its distinguishing characteristics through succeeding propagations by budding.

*Flower*

Locality where grown: West Grove, Pennsylvania.

Flowers borne: Singly on normal, long stems.

Quantity of bloom: Free outdoors.

Continuity: Intermittent.

Fragrance: Slight moderate carnation fragrance.

Bud:

*Peduncle.*—Long; slender; erect; light; numerous; Garnet Brown, Plate 1; hairs, Morocco Red, Plate 1.

*Before calyx breaks.*—Size—medium. Form—long, pointed with a conspicuous neck, with foliaceous appendages on the surface of the bud; with slender, bristle-like foliaceous parts extending beyond the tip of the bud equal to ¾ of its length.

*As calyx breaks.*—Color Oxblood Red to Carmine, Plate 1.

*As first petal opens.*—Size—medium. Form—long; flat. Color—outside—Pomegranate Purple to Rose Red, Plate XII; inside—Vivid Rose Red, Plate XII. Opening—opens up well.

Bloom:

*Size.*—When fully open, large; 5″ to 5½″.

*Petalage.*—Double (stamens not hidden); from 25 to 30 petals, arranged irregularly.

*Form.*—Open, high center at first; becoming cactus form; petals, remaining at first, loosely rolled outward; becoming later, at maturity, very loosely rolled outward.

Petals: Leathery; soft; with inside velvety and outside satiny.

*Shape.*—Outside—obovate with apex flat. Intermediate—ovate with apex flat. Inside—obovate with apex flat.

The following description of a newly opened flower was made from a rose grown outdoors in October 1940, at West Grove, Pennsylvania:

*Color.*—*Outside petal*—outside surface—Pomegranate Purple to Rose Red, Plate XII; inside surface—Rose Red, Plate XII. *Intermediate petal*—outside surface—Light Oxblood Red to Carmine, Plate 1; inside surface—Vivid Rose Red, Plate XII. *Inner petal*—outside surface—Oxblood Red to Carmine, Plate 1; inside surface—Vivid Rose Red, Plate XII.

The following description was made from a rose open for three days outdoors in October 1940, at West Grove, Pennsylvania:

*Color.*—*Outside petal*—Outside surface—Begonia Rose, Plate 1; inside surface—Eugenia Red, Plate XIII. *Inside petal*—outside surface—Carmine, Plate 1; inside surface—Carmine to Spectrum Red, Plate 1.

*General color effect.*—Newly opened flower—Spectrum Red to Carmine, Plate 1. Three days open—Begonia Rose, Plate 1.

*Behavior.*—Drop off cleanly; fading Tyrian Rose, Plate XII.

*Flower longevity.*—On bush in garden 3 to 5 days in October; as cut roses grown outdoors, 6 to 7 days in October.

*Reproductive organs*

Stamens: Medium number, arranged irregularly about pistils, mixed with petaloids, tucked in calyx.

Filaments: Medium length; Carmine, Plate 1; most with anthers.
Anthers: Medium size; Ochraceous Buff, Plate XV; open at various times.
Pollen: Buff, Plate IV.
Pistils: Many.
Styles: Uneven: long; thin; loosely bunched.
Stigma: White.
Ovaries: All enclosed in calyx.
Hips: Short; globular, with conspicuous neck; Cerro Green, Plate V; smooth; walls thick, fleshy.
Sepals: Falling soon; moderately long; spear-shaped; recurved.
Seeds: Few; small.

*Plant*

Foliage: 3 to 7 leaflets; normal; large; leathery; glossy.
*Leaflets.*—Ovoid with apex mucronate; base obtuse; margin simply serrate.
*Color.*—*Mature*—upper surface—Dark Yellow Green, Plate XXXII; under surface—Light Grass Green, Plate XXXI. *Young*—upper surface—Olive, Plate XXX, shaded Maroon, Plate 1; Under surface—Buffy Olive, Plate XXX, shaded Mahogany Red, Plate 11.
*Rachis.*—Medium weight. Upper side, smooth, grooved; under side, smooth.

*Stipules.*—Short; narrow; with short points turning out at an angle of less than 90°, recurved toward the stem.
*Stipules.*—Resistant to mildew, and black-spot.
Growth:
*Habit.*—Upright, branched.
*Growth.*—Vigorous.
*Canes.*—Moderately heavy.
*Main stems.*—Bright; Oxblood Red, Plate 1. *Thorns*—several; medium length; hooked downward; with medium base. *Prickles*—none. *Hairs*—none.
*Branches.*—Bright; Oxblood Red, Plate 1. *Thorns*—Few; medium length; hooked downward; with medium base. *Prickles*—none. *Hairs*—none.
*New shoots.*—Bright; Oxblood Red, Plate 1. *Thorns*—few; medium length; hooked downward with medium base. *Prickles*—none. *Hairs*—none.

I claim:

A new and distinct variety of rose plant of the class of hybrid teas, characterized as to novelty by the color combination and size of its flowers, length of bud, strength of stems, and good vegetative habit, substantially as herein disclosed.

MARGUERITE KETTEN,
*Marguerite Ketten, Executrix of the Estate of Charles Ketten, Deceased.*